(12) United States Patent
Lorenz et al.

(10) Patent No.: US 7,056,352 B2
(45) Date of Patent: Jun. 6, 2006

(54) COMPOSITION FOR THE DYEING OF HUMAN HAIR

(75) Inventors: Heribert Lorenz, Gross-Bieberau (DE); Klaus Kaffenberger, Alsbach-Haehnlein (DE); Bernd Noecker, Ober-Ramstadt (DE); Ruediger Wilz, Pfungstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 158 days.

(21) Appl. No.: 10/465,255

(22) Filed: Jun. 19, 2003

(65) Prior Publication Data
US 2004/0006833 A1 Jan. 15, 2004

(30) Foreign Application Priority Data
Jul. 11, 2002 (DE) ................. 102 31 260

(51) Int. Cl.
*A61K 7/13* (2006.01)
(52) U.S. Cl. ................. 8/405; 8/406; 8/408; 8/410; 8/411; 8/421
(58) Field of Classification Search ................. 8/405, 8/406, 408, 410, 411, 421
See application file for complete search history.

(56) References Cited

U.S. PATENT DOCUMENTS 4,865,619 A * 9/1989 Junino et al. ................. 8/412
5,514,188 A * 5/1996 Cotteret et al. ................. 8/412
5,578,087 A * 11/1996 Audousset et al. ............. 8/409
5,672,759 A * 9/1997 Junino et al. ................ 564/440
5,863,300 A * 1/1999 Audousset et al. ............. 8/411

FOREIGN PATENT DOCUMENTS

| DE | 38 18 139 A1 | 12/1988 |
| DE | 693 09 638 T2 | 7/1997 |
| DE | 198 34 567 C1 | 2/2000 |
| DE | 200 17 642 U1 | 1/2001 |
| DE | 100 51 034 A1 | 4/2002 |
| DE | 101 18 892 A1 | 10/2002 |

* cited by examiner

Primary Examiner—Eisa Elhilo
(74) Attorney, Agent, or Firm—Norris McLaughlin & Marcus PA

(57) ABSTRACT

Hair dyeing composition on the basis of an oxidation dyestuff precursor reacting with peroxide, comprising at least one developing and/or coupling substance selected from the group
a) 3-chloro-p-aminophenol and
b) 2-methyl-5-γ-hydroxypropyl aminophenol, 2-methyl-5-methyl aminophenol, 2-methyl-5-ethyl aminophenol, 2-methoxy-5-aminophenol, 2-methyl-4-methoxy-5-aminophenol and/or 2-methyl-4-methoxy-5-hydroxyethyl aminophenol and
c) 1-methoxy-2,4-diaminobenzene, 1-β-hydroxyethyloxy-2,4-diaminobenzene, 1-(1,2-dihydroxypropyloxy)-2,4-diaminobenzene, 1-methoxy-2-amino-4-β-hydroxyethyl aminobenzene, 1,3-bis-(2,4-diaminophenoxy)-propane, 2,4-diamino-5-methylphenetol and/or 1-β-hydroxyethyloxy-5-methyl-2,4-diaminobenzene.

4 Claims, No Drawings

COMPOSITION FOR THE DYEING OF HUMAN HAIR

The present invention concerns a composition for the dyeing of human hair on the basis of an oxidation dyestuff precursor system reacting with peroxide which provides long-lasting, intensive colors either used as such, or which can be used to obtain further shades in combination with additional developing and/or coupling agents and which does not damage the hair even upon repeated application within short intervals.

The developing substances still most frequently used in hair dyeing compositions are 1,4-diaminobenzene (p-phenylenediamine) and 1-methyl-2,5-diaminobenzene (p-toluylenediamine). Although incorporation of these substances largely fulfills the user's color wishes, there are still shades that cannot be completely achieved by the use thereof.

Proposals have also been made to close this gap by the use of alternative developing substances. To a limited degree this is possible with the use of tetraaminopyrimidine or 2-(2,5-diaminophenyl)ethanol (see and EP-B 400 330); however, it is then necessary to accept reduced color intensity in other shades. A further satisfactory solution of this problem is disclosed in EP-A 615 743, with the use of 2-(2'-hydroxyethyl amino)-5-aminotoluene or the water-soluble salts thereof, as a component of oxidation hair dye compositions.

However, to the present it has not been possible to achieve strong colorations in the range of red by this means.

The invention starts from the task of counteracting this deficiency and providing an oxidation dyestuff composition which achieves intensive, glossy colorations, especially in the range of red, and which leaves the hair without damage even upon repeated application within short periods of time.

This task is solved when such a hair dyeing composition comprises an oxidation dyestuff system reacting with peroxide which is selected from a) 3-chloro-p-aminophenol and b) 2-methyl-5-γ-hydroxypropyl aminophenol, 2-methyl-5-methyl aminophenol, 2-methyl-5-ethyl aminophenol, 2-methoxy-5 aminophenol, 2-methyl-4-methoxy-5-aminophenol and/or 2-methyl-4-methoxy-5-hydroxyethyl amino-phenol and c) 1-methoxy-2,4-diaminobenzene, 1-β-hydroxyethyloxy-2,4-diamino-benzene, 1-(1,2-dihydroxypropyloxy)-2,4-diaminobenzene, 1-methoxy-2-amino-4-β-hydroxyethyl aminobenzene, 1,3-bis-(2,4-diaminophenoxy)-propane, 2,4-diamino-5-methyl-phenol and/or 1-β-hydroxyethyloxy-5-methyl-2,4-diaminobenzene.

After oxidation with peroxide, use of these compositions on the basis of a customary carrier provides very expressive, intensive, long-lasting hair colorations, especially in the range of red, which can be varied to achieve further shades by the addition of the respective further developing and coupling substances.

In addition to the named developing and coupling substances it is also possible to incorporate further substances of this type. Further suitable coupling substances are, for example, 1-methoxy-2-amino-4-(β-hydroxyethyl amino) benzene, 2-amino-3-hydroxypyridine, 3-amino-2-methylamino-6-methoxypyridine, resorcinol, 2-methyl resorcinol, 4-chlororesorcinol, 1,3-diamino benzene, 1,6-dihydroxynaphthaline, 1,7-dihydroxy-naphthaline, p-phenylenediamine, p-toluylenediamine, 2,6-dimethyl-p-phenylenediamine, 2-hydroxymethyl-p-phenylenediamine, 2-hydroxyethyl-p-phenylenediamine, 2-n-propyl-p-phenylenediamine, N,N-bis(β-hydroxyethyl)-p-phenylenediamine, N-methoxyethyl-p-phenylenediamine and/or 5-chloro-2-hydroxyethyl-p-phenylenediamine or the water-soluble salts thereof.

The total concentration of the developing substances is customarily from 0.05% to 5%, preferably 0.1% to 4%, in particular 0.5% to 3% by weight, calculated to the total hair dyeing composition (excluding the oxidation agent), whereby these figures are always related to the proportion of free base. The preferred weight proportion of the developing substances to the additional developing and coupling substances range between about 1:8 to 8:1, preferably about 1:5 to 5:1, in particular 1:2 to 2:1.

In the hair dyeing compositions according to the invention, the coupling substance(s) as reaction partners of the developing substance(s) are present in approximately the same molecular proportions as the developing substances, i.e. in amounts from 0.05% to 5.0%, preferably 0.1% to 4%, in particular 0.5% to 3% by weight, calculated to the total composition (excluding the oxidizing agent), whereby these figures are always related to the proportion of free base.

If desired, the compositions according to the invention can also contain so-called shading agents for precise adjustment of the desired shade, in particular direct-acting dyestuffs.

Such shading agents are, for example, nitro dyestuffs such as 2-amino-4,6-dinitrophenol, 2-amino-4-nitrophenol, 2-amino-6-chloro-4-nitrophenol, etc., preferably in amounts from about 0.05% to 2.5%, in particular 0.1% to 1% by weight of the dyestuff composition (excluding the oxidizing agent).

The hair dyeing compositions according to the invention can comprise the basic substances and additives customarily found in such compositions, conditioning agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815. They can be prepared as solutions, creams, gels or also in the form of aerosol products; suitable carrier material compositions are known as state of the art.

For application, the oxidation dyestuff precursor is mixed with an oxidizing agent. The preferred oxidizing agent is hydrogen peroxide, for example in a concentration of 2% to 6% by weight.

However, the use of other peroxides such as urea peroxide and melamine peroxide is also possible.

The pH-value of the ready-to-use hair dyeing composition, i.e. after mixing with peroxide, can be in a slightly acidic range, i.e. from 5.5 to 6.9, as well as in the neutral or alkaline range, i.e. between pH 7.1 and 10.

In the following, various Examples are used to illustrate the invention.

| Carrier | |
|---|---|
| Stearyl alcohol | 8.0 (% by wt.) |
| Coco fatty acid monoethanolamide | 4.5 |
| 1,2-Propanediol mono/distearate | 1.3 |
| Coco fatty alcohol polyglycol ether | 4.0 |
| Sodium lauryl sulfate | 1.0 |
| Oleic acid | 2.0 |
| 1,2-Propanediol | 1.5 |
| Na-EDTA | 0.5 |
| Sodium sulfite | 1.0 |
| Protein hydrolyzate | 0.5 |
| Ascorbic acid | 0.2 |
| Perfume | 0.4 |
| Ammonia, 25% | 1.0 |

-continued

| Carrier | |
|---|---|
| Ammonium chloride | 0.5 |
| Panthenol | 0.8 |
| Water | ad 100.00 |

The oxidation dyestuff combinations according to the invention were incorporated into this carrier, whereby the water content was reduced accordingly.

The colorations were carried out on wool patches and strands of bleached human hair by application of a 1:1 mixture of a dyestuff precursor and a 6% hydrogen peroxide solution (pH-value of the mixture: 9.8) with twenty minutes processing at room temperature, subsequent rinsing and drying.

The following colorations were achieved:

Example 1:

| 0.21 | (% by wt.) | 3-Chloro-p-aminophenol HCl |
| 0.14 | | 2-Methyl-5-γ-hydroxypropyl aminophenol |
| 0.27 | | 1-β-Hydroxyethyloxy-2,4-diaminobenzene HCl |
| 0.20 | | 1-Phenyl-3-methyl-5-pyrazolone |

Coloration:

Brilliant beige-red.

Example 2:

| 0.41 | (% by wt.) | 3-Chloro-p-aminophenol HCl |
| 0.14 | | 2-Methyl-5-γ-hydroxypropyl aminophenol |
| 0.31 | | 1-Methoxy-2-amino-4-β-hydroxyethyl aminobenzene $H_2SO_4$ |

Coloration:

Brilliant carmine red.

Example 3:

| 0.41 | (% by wt.) | 3-Chloro-p-aminophenol HCl |
| 0.145 | | 2-Methyl-5-γ-hydroxypropyl aminophenol |
| 0.49 | | 1,3-Bis-(2,4-diaminophenoxy)-propane 4HCl |

Coloration

Brilliant mahogany-red.

Example 4:

| 0.41 | (% by wt.) | 3-Chloro-p-aminophenol HCl |
| 0.09 | | 2-Methyl-5-γ-hydroxypropyl aminophenol |
| 0.21 | | 1-Methoxy-2-amino-4β-hydroxyethyl amino benzene |
| 0.33 | | $H_2SO_4$ 1,3-Bis-(2,4-diaminophenoxy)-propane 4HCl |

-continued

Coloration:

Brilliant mahogany-violet.

Example 5:

| 0.41 | (% by wt.) | 3-Chloro-p-aminophenol HCl |
| 0.19 | | 2-Methyl-5-γ-hydroxypropyl aminophenol |
| 0.27 | | 1-β-Hydroxyethyloxy-2,4-diaminobenzene HCl |

Coloration:

Brilliant beige-red-orange.

Example 6:

| 0.41 | (% by wt.) | 3-Chloro-p-aminophenol HCl |
| 0.14 | | 2-Methyl-5-γ-hydroxypropyl aminophenol |
| 0.27 | | 1-β-Hydroxyethyloxy-2,4-diaminobenzene HCl |

Coloration:

Brilliant beige-red-orange.

The invention claimed is:

1. Hair dyeing composition on the basis of an oxidation dyestuff precursor reacting with peroxide, which contains developing and coupling substance(s) comprising
   a) 3-chloro-p-aminophenol;
   b) at least one compound selected from the group consisting of: 2-methyl-5-γ-hydroxypropyl aminophenol, 2-methyl-5-methyl aminophenol, 2-methyl-5-ethyl aminophenol, 2-methoxy-5-aminophenal, 2-methyl-4-methoxy-5-aminophenol and 2-methyl-4-methoxy-5-hydroxyethyl aminophenol; and
   c) at least one compound selected from the group consisting of 1-methoxy-2,4-diaminobenzene, 1-β-hydroxyethyloxy-2,4-diaminobenzene, 1-(1,2-dihydroxypropyloxy)-2,4-diaminobenzene, 1-methoxy-2-amino-4-β-hy-droxyethyl aminobenzene, 1,3-bis-(2,4-diaminophenoxy)-propane, 2,4-diamino-5-methyl-phenol and/or 1-β-hydroxyethyloxy-5-methyl-2,4-diaminobenzene wherein said developing and/or coupling substance(s) includes salt forms thereof and said hair dyeing composition produces hair colorations in the range of red.

2. The hair dyeing composition of claim 1 wherein the total concentration of the developing substance is from 0.05% to 5% by weight, calculated from the total weight of the hair dyeing composition excluding the oxidation agent.

3. The hair dyeing composition of claim 1 which further comprises of a shading agent in an amount of from about 0.05% to about 2.5% by weight based on the total weight of the hair dyeing composition (excluding the oxidizing agent).

4. The hair dyeing composition of claim 3 wherein the shading agent is a nitro dyestuff.

* * * * *